United States Patent [19]

Albrecht et al.

[11] 4,078,070
[45] Mar. 7, 1978

[54] FUNGICIDAL DISPERSIONS

[75] Inventors: Konrad Albrecht; Heinz Frensch, both of Frankfurt am Main; Kurt Hartel; Helmut Stingl, both of Hofheim, Taunus, all of Germany

[73] Assignee: Hoechst Aktiengesellschaft, Frankfurt am Main, Germany

[21] Appl. No.: 611,788

[22] Filed: Sep. 9, 1975

Related U.S. Application Data

[63] Continuation of Ser. No. 432,825, Jan. 14, 1974, abandoned.

[30] Foreign Application Priority Data

Jan. 16, 1973 Germany ............................ 2301921

[51] Int. Cl.² .......................... A01N 9/22; A01N 9/28
[52] U.S. Cl. .................................... 424/273 R; 424/285
[58] Field of Search ................................. 424/273, 285

[56] References Cited

U.S. PATENT DOCUMENTS 3,293,123  12/1966  Speziale et al. ..................... 424/283
3,660,421  5/1972  Osieka ................................. 424/273
3,784,571  1/1974  Dodds ................................. 424/273

FOREIGN PATENT DOCUMENTS 6,706,331  11/1967  Netherlands.
1,194,526  6/1970  United Kingdom ............. 260/345.7

OTHER PUBLICATIONS

Chem. Abst. 65 18,839(d) (1966), Bogatyrew et al., "Use of Aging Inhibitors in . . .".

*Primary Examiner*—Albert T. Meyers
*Assistant Examiner*—D. W. Robinson
*Attorney, Agent, or Firm*—Curtis, Morris & Safford

[57] ABSTRACT

Dispersions of 2-methyl-5,6-dihydropyran-3-carboxylic acid anilide and benzimidazole-2-carbamic acid methyl ester or 1-n-butylcarbamoyl-benzimidazole-2-carbamic acid methyl ester in paraffinic mineral oils, liquid triglycerides and/or liquid esters of $C_1$ to $C_{12}$ monoalcohols have a synergistic effect against rust and other fungus diseases. The dispersions are stabilized against crystal growth by adding aluminum chelates of certain hydroxy-quinones, e.g., alizarin.

8 Claims, No Drawings

FUNGICIDAL DISPERSIONS

This is a continuation of application Ser. No. 432,825, filed Jan. 14, 1974, and now abandoned.

The present invention relates to fungicidal dispersions containing as active ingredients 2-methyl-5,6-dihydropyran-3-carboxylic acid anilide and benzimidazole-2-carbamic acid methyl ester or 1-n-butyl-carbamoyl-benzimidazole-2-carbamic acid methyl ester.

2-Methyl-5,6-dihydropyran-3-carboxylic acid anilide (I), benzimidazole-2-carbamic acid methyl ester (II) and 1-n-butyl-carbamoyl-benzimidazole-2-carbamic acid methyl ester (III) are known fungicides (cf. Belgian Pat. No. 727,245, German Offenlegungsschrift No. 1,620,175 and Netherlands Offenlegungsschrift No. 67,06331).

It has now been found that mixtures of the active ingredients I and II or I and III, respectively, in the form of dispersions in mineral or vegetable oils and other organic liquids not being phytotoxic, exhibit a strongly improved synergistic effect as compared with the effect of the individual compounds against rust and other fungus diseases. They are especially characterized by an excellent efficiency against diseases caused by Colletotrichum species.

The present invention therefore provides fungicidal dispersions of 2-methyl-5,6-dihydropyran-3-carboxylic anilide (I) with benzimidazole-2-carbamic acid methyl ester (II) or with 1-n-butylcarbamoyl-benzimidazole-2-carbamic acid methyl ester (III) comprising paraffinic mineral oils, liquid triglycerides and/or liquid esters $C_1$ to $C_{12}$ monoalcohols and an aluminum chelate compound as stabilizer and optionally in combination with further usual formulation auxiliaries.

In the dispersions according to the invention the proportions of active compounds I and II or I and III are preferably in the range of from 3 : 1 to 1 : 3, more preferably 1.5 : 1 to 1 : 3, especially good results being obtained with proportions of 1.5 : 1 to 1 : 1.5.

Suitable dispersion media for the dispersions of the invention are, for example, (1) straight chain or branched $C_8$ to $C_{25}$ paraffins having boiling points above 140° C, preferably above 260° C, for example nonane, decane, undecane, dodecane, tridecane, tetradecane, pentadecane, hexadecane, or mixtures thereof with higher boiling homologs, such as hepta-, octa-, nonadecane, eicosane, heneicosane, docosane, tricosane, tetracosane, pentacosane, and the branched chain isomers thereof;

(2) liquid triglycerides, for example vegetable oils such as rape-seed oil, arachis oil, sunflower oil, cotton seed oil;

(3) liquid esters of $C_1$ to $C_{12}$ monoalcohols with $C_2$ to $C_{10}$ carboxylic acids, such esters containing at least 8 and in the case of esters of monobasic acids at most 12 carbon atoms and in the case of esters of dibasic acids at most 32 carbon atoms. Suitable esters are, for example, those of aliphatic $C_6$ to $C_{10}$ carboxylic acids, for example caproic acid, capric acid, caprylic acid and pelargonic acid; or of aromatic carboxylic acids such as benzoic acid, toluylic acid, salicylic acid and phthalic acid. Suitable alcohol components in these esters are, for example butanol, n-octanol, i-octanol, dodecanol, cyclopentanol, cyclohexanol, cyclooctanol, or benzyl alcohol. Esters to be used in the dispersions of the invention are thus, for example, benzyl acetate, caproic acid ethyl ester, polargonic acid ethyl ester, benzoic acid methyl or ethyl ester, salicylic acid methyl, propyl, or butyl ester, preferably, however, diesters of phthalic acid with saturated aliphatic or alicyclic $C_1$ to $C_{12}$ alcohols, such as phthalic acid dimethyl ester, dibutyl ester, diisooctyl ester, didodecyl ester, dicyclopentyl ester, dicyclohexyl ester, or dicyclooctyl ester.

The dispersions of the invention are prepared by known methods by grinding the active compounds dispersed in the dispersion medium in a colloid mill, ball mill, sand mill, and preferably in grinding ball mills, optionally with the addition of further usual formulation auxiliaries such as emulsifiers, dispersion media, wetting agents or adhesives.

The content of active ingredient of the dispersions is in the range of from 5 to 50% by weight, preferably 15 to 30% by weight. Highly concentrated dispersions containing 50% by weight of active ingredient or slightly less are used as ultra low volume (ULV) preconcentrates. They may contain further additions of formulation auxiliaries but are unsuitable for direct application owing to their high viscosity; rather they are diluted prior to application. Suitable diluents for this purpose are, in the first place, the mineral oil, triglyceride or ester used for preparing the dispersion to which emulsifiers, wetting agents, adhesives, or dispersions media may be added according to the requirements in each case. It is also possible, of course, to use mixtures of mineral oils, triglycerides and/or esters for making dispersions ready for application. In general, the proportion of emulsifiers and dispersion media in the total dispersion is below 20%, wetting agents and adhesives can be added to the dispersion in an amount of up to about 5%.

Suitable emulsifiers and dispersion media are substituted alkylphenol polyglycol ethers, such as octyl-, nonyl-, or triisobutylphenol polyglycol ether, natural fatty alcohol polyglycol ethers as well as polyglycol ethers of synthetic alcohols, preferably isotridecanol polyglycol ether, fatty acid polyglycol esters, and mixtures of ethoxylated substances, optionally in combination with calcium salts of alkyl-benzene or paraffin-sulfonic acids and chlorinated paraffin-sulfonic acids.

Suitable wetting agents are, for example, emulsifiers such as oxethylated alkylphenols, salts of alkyl- or arylsulfonic acids or salts of oleylmethyl tauride.

The dispersions in accordance with the invention are readily pourable in the preferred range of from 15 to 30% of active ingredient, their viscosity in the range of application is below 5, preferably below 3 poises, depending on the content of active ingredient, and they can be dispersed both in water or paraffin oils in any desired proportion. Depending on the degree of dilution, they can be applied according to the low volume or ultra low volume process by aeroplanes or with soil application devices.

Owing to the fact that crystals of 2-methyl-5,6-dihydropyran-3-carboxylic acid anilide have a pronounced tendency to grow when in the form of a dispersion (a sample in which the active compound was ground to a particle size of less than 10 microns contained crystals of a length of over 100 microns after a four week storage at 50° C) a stabilizer should preferably be added to the dispersions to obtain the required stability in storage, especially if the formulation is destined for use in tropical countries or for prolonged shipment. Surprisingly, an excellent stability in storage can be obtained by adding to the dispersions aluminum chelate compounds of aromatic polynuclear quinones containing hydroxy groups in alpha and preferably in peri-position to an oxygen atom of the quinone grouping, such as naphthazarin, quinizarin, chrysazim, and preferably alizarin. Chelates of this type generally contain the atom grouping

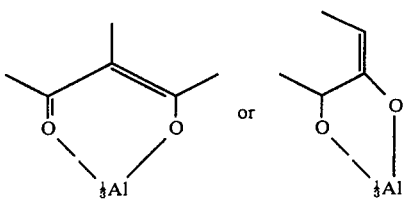

The preparation of aluminum chelates is described in Chemische Berichte 46, pages 451, et seq. The addition of chelates of this type strongly reduces crystal growth. In a test of long duration at 50° C the particles still had a particle size below 10 microns on the average even after a 2 month storage. A storage under these conditions generally corresponds to a storage for 2 years at normal temperature.

The amounts of aluminum chelate necessary for stabilizing the oil dispersions of the invention are, in general, in the range of from about 0.2 to about 5% by weight, preferably 0.4 to 1% by weight, calculated on the total formulation. Amounts higher than 5% may also be added, but offer no additional advantage.

Aluminum chelate compounds can be added to the dispersion either per se or in the form of their starting components (aluminum salts or aluminum hydroxide, preferably aluminum acetate, and an aromatic quinone, preferably alizarin) prior to its preparation. In the latter case the chelate compounds are formed during the grinding of the formulation components, which in the case of alizarin can be perceived by the change in color from yellow orange to red. When the starting components are used aluminum compound and quinone are added in stoichiometric amounts or, for the sake of simplicity, in equal amounts by weight.

Owing to their long stability in storage at +50° C the dispersions according to the invention comply with international standards and ensure a reliable application and safe combating result.

The following examples illustrate the invention.

EXAMPLES OF PREPARATION

EXAMPLE 1

(comparative example)

In a grinding ball mill operated with quartz beads having a diameter of 1 to 2 mm the following mixture was ground until the particles had a size of less than 5 microns:
10% by weight of 2-methyl-5,6-dihydropyran-3 carboxylic acid anilide
10% by weight of benzimidazole-2-carbamic acid methyl ester
6% by weight of alkyl-phenol polyglycol ether (Triton ®X 207 Rohm & Haas)
3% by weight of isotridecanol polyglycol ether (Genapol ®X-080 Hoechst) and
71% by weight of paraffinic mineral oil (Essobayol 90 of Esso Ag).

The formulation was readily pourable and dispersible in water and other paraffin oils. During storage a rapid crystal growth was observed. When stored at 50° C, the product contained after 4 weeks crystals of a length of over 150 microns. The formulation was then useless.

EXAMPLE 2

The following mixture was ground in the mill of Example 1:
10% by weight of 2-methyl-5,6-dihydropyran-3-carboxylic acid anilide
10% by weight of benzimidazole-2-carbamic acid methyl ester
8% by weight of alkyl-phenol polyglycol ether (Triton ®X-207)
4% by weight of isotridecanol polyglycol ether (Genapol ®X-080)
0.5% by weight of aluminum chelate of alizarin and
67.5% by weight of paraffinic mineral oil (Essobayol 90 of Esso AG)

After a 2 month storage at 50° C, only a few crystals having a length of at most 12 microns could be detected.

The biological activity of the stored product was equal to that of the freshly prepared product.

EXAMPLE 3

In the manner described in Example 1 the following mixture was ground:
10% by weight of 2-methyl-5,6-dihydropyran-3-carboxylic acid anilide
10% by weight of benzimidazole-2-carbamic acid methyl ester
25% by weight of paraffinic mineral oil (Isopar G, BP AG)
34% by weight of rape seed oil
10% by weight of castor oil polyglycol ether (EmulsogenT ®, Hoechst)
10% by weight of oleyl alcohol polyglycol ether (Emulsogen M ®, Hoechst)
1% by weight of aluminum chelate of alizarin.

During storage the crystal conditions of the dispersion did not change. After a storage of 2 months at 50° C the particle size distribution distribution was still the same as in the dispersion of Example 2.

EXAMPLE 4

In the manner described in Example 1 the following mixture was ground:
10% by weight of 2-methyl-2,5-dihydropyran-3-carboxylic acid anilide
10% by weight of benzimidazole-2-carbamic acid methyl ester
12% by weight of mixed emulsifier composed of calcium dodecyl benzene-sulfonate and castor oil polyglycol ether (Emulsogen IP 400, Hoechst)
6% by weight of alkyl-phenol polyglycol ether (Triton ®X-207)
0.5% by weight of aluminum chelate of alizarin
61.5% by weight of phthalic acid diisooctyl ester By the addition of the aluminum chelate of alizarin the crystal growth could be avoided during storage. After a 2 month storage at 50° C only a few crystals having a length of 15 microns could be observed.

EXAMPLE 5

In the manner described in Example 1, the following mixture was ground:
10% by weight of 2-methyl-5,6-dihydropyran-3-carboxylic acid anilide
10% by weight of 1-n-butyl-carbamoyl-benzimidazole-2-carbamic acid methyl ester 10% by weight of alkyl-phenol polyglycol ether (Triton ®X-207)
5% by weight of isotridecanol polyglycol ether (Genapol ®X-080)
1% by weight of aluminum chelate of alizarin
54% by weight of paraffinic mineral oil (Essobayol 90)

After a storage under the conditions of Example 4 in this case, too, an insignificant growth could only be observed (a few crystals having a length of 14 microns).

When in Examples 2 to 5 the alizarin component was omitted crystal growth occurred as in Example 1.

EXAMPLE 6

In a manner described in Example 1, the following mixture was ground:
15% by weight of 2-methyl-5,6-dihydropyran-3-carboxylic acid anilide
15% by weight of benzimidazole-carbamic acid methyl ester
10% by weight of alkyl-phenol polyglycol ether (Triton ®X-207)
5% by weight of isotridecanol polyglycol ether (Genapol ®X-080)
53% by weight of paraffinic mineral oil (Shellsol K®).
1% by weight of chrysazin
1% by weight of basic aluminum acetate.

After a 2 month storage at 50° C, the particles of the formulation had grown little only. A few crystals had a length of from 10 to 15 microns.

The following biological examples demonstrate the efficiency of the mixtures as compared to the individual components, the degree of infestation of untreated plants being equal to 100. The applied concentrations of the mixtures refer to the sum of the active compounds I + II or I + III.

BIOLOGICAL EXAMPLES

EXAMPLE I

Wheat plants in the three leaf stage were strongly infested with spores of brown rust and placed for 1 day in a chamber at a temperature of 20° C and 100% of relative humidity. Subsequently, the infested plants were transferred into the greenhouse and 5 days after infestation the plants were sprayed to the drip off with aqueous dispersions of the formulations of Examples 2 to 5 in a concentration of 300, 150, 75 and 36 mg of active compound(s) per liter of spray liquor.

For comparison the individual components I, II and III were used in the form of oil dispersions containing 20% of active compound, prepared as described in Example 1, the concentrations applied being the same as above.

After a time of incubation of 14 days, the plants were examined as to the degree of infestation with brown rust. The results, expressed in % of infested leaf area, calculated on untreated infested plants, are listed in Table I.

TABLE I

| Formulation according to Example | % leaf surface infested with brown rust with mg of active compound(s) per liter of spray liquor | | | |
|---|---|---|---|---|
| | 300 | 150 | 75 | 36 |
| 2 | 0 | 0 | 0 | 10 |
| 3 | 0 | 0 | 0 | 12 |
| 4 | 0 | 0 | 0 | 10 |
| 5 | 0 | 0 | 0 | 18 |
| compound I | 0 | 0 | 5 | 15 |
| compound II | 15 | 28 | 40 | 65 |
| compound III | 15 | 25 | 42 | 65 |

TABLE I-continued

| Formulation according to Example | % leaf surface infested with brown rust with mg of active compound(s) per liter of spray liquor | | | |
|---|---|---|---|---|
| | 300 | 150 | 75 | 36 |
| untreated infested plants | 100 | | | |

EXAMPLE II

Wheat plants were sprayed to the drip off with aqueous dispersions of the formulations according to Examples 2 to 5 and formulations of the individual active components in concentrations of 300, 150, 75, 36 and 18 mg of active compound(s) per liter of spray liquor.

After drying of the coating containing the active ingredient, the plants were strongly infested with spores of brown rust and placed drip wet for one day in a chamber having a temperature of 20° C and a relative humidity of 100%. Subsequently, the plants were transferred to the greenhouse and 14 days after infestation they were examined as to the degree of infestation with brown rust.

The results are listed in Table II

TABLE II

| Formulation according to Example | % leaf surface infested with brown rust with mg of active compound(s) per liter of spray liquor | | | | |
|---|---|---|---|---|---|
| | 300 | 150 | 75 | 36 | 18 |
| 2 | 0 | 0 | 0 | 0 | 5 |
| 3 | 0 | 0 | 0 | 0 | 7 |
| 4 | 0 | 0 | 0 | 0 | 6 |
| 5 | 0 | 0 | 0 | 0 | 10 |
| compound I | 0 | 0 | 5 | 10 | 20 |
| compound II | 25 | 35 | 50 | 75 | 100 |
| compound III | 20 | 35 | 40 | 70 | 95 |
| untreated infested plants | 100 | | | | |

EXAMPLE III

Plants of Coffea arabica were cultivated in the greenhouse and strongly infested with spores of coffee rust (Hemileia vastatrix) after having reached a height of 15 cm. Subsequently, the plants were placed drip wet for 3 days in a chamber having a temperature of 22° C and a relative humidity of 100%. The plants were then transferred to the greenhouse having a temperature of 22° C and a relative humidity of 85–95% and 5 days after infestation they were sprayed to the drip off with the formulations of Examples 2 to 5 and formulations of the individual compounds, the concentrations being 600, 300, and 150 mg of active compound(s) per liter of spray liquor. After drying of the coating containing the active ingredient the plants were placed again into the greenhouse.

After a time of incubation of 35 days, the plants were examined as to their degree of infestation with coffee rust by visual inspection in comparison to untreated infested control plants. The results are listed in Table III.

TABLE III

| formulation according to Example | % of infestation with coffee rust with mg of active compound(s) per liter of spray liquor | | |
|---|---|---|---|
| | 600 | 300 | 150 |
| 2 | 0 | 0 | 5 |
| 3 | 0 | 0 | 6 |
| 4 | 0 | 0 | 5 |
| 5 | 0 | 0 | 8 |

TABLE III-continued

| formulation according to Example | % of infestation with coffee rust with mg of active compound(s) per liter of spray liquor | | |
|---|---|---|---|
| | 600 | 300 | 150 |
| compound I | 0 | 0 | 16 |
| compound II | 15 | 35 | 50 |
| compound III | 15 | 30 | 45 |
| untreated infested plants | | 100 | |

EXAMPLE IV

A suspension of spores of *Colletotrichum coffeanum* was stirred for 15 minutes with an equal volume of a suspension of a combination of active compounds I and II or I and III, respectively, in the form of the formulations of Examples 2 to 5, the concentrations applied being 0.03, 0.015, 0.0075, 0.0036, and 0.0018% by weight. The spore suspensions obtained were spread on agar plates. In the same manner the individual compounds I, II, and III were tested in the form of oil dispersions of 20% strength in the same concentrations with respect to the active compound. For each concentration 4 tests were run.

The inoculated plates were incubated in a thermostat for 5 days at 22° C and then examined as to the growth of the fungus. The result is listed in Table IV.

TABLE IV

| Formulation according to Example | germination of spores and growth of mycelium with % by weight of active compound(s) expressed in figures from 0 to 4 | | | |
|---|---|---|---|---|
| | 0.03 | 0.015 | 0.0075 | 0.0036 |
| 2 | 0 | 0 | 0 | 1 |
| 3 | 0 | 0 | 0 | 1 |
| 4 | 0 | 0 | 0 | 1 |
| 5 | 0 | 0 | 0 | 1 |
| compound I | 2 | 3 | 4 | 4 |
| compound II | 0 | 0-1 | 1-2 | 3 |
| compound III | 0 | 0-1 | 1-2 | 2-3 |
| untreated | 4 | 4 | 4 | 4 |

Meaning of the figures:
0 no germination of spores, no growth of mycelium
1 weak but strongly hindered growth of mycelium
2 weak growth of mycelium
3 moderately hindered growth of mycelium
4 strong unhindered growth of mycelium

What is claimed is:

1. A fungicidal dispersion comprising 5 to 50% by weight of 2-methyl-5,6-dihydropyran-3-carboxylic acid anilide in combination with either benzimidazole-2-carbamic acid methyl ester in a proportion from 1.5:1 to 1:1.5 or 1-n-butyl-carbamoyl-benzimidazole-2-carbamic acid methyl ester in proportions from 1.5:1 to 1:1.5 and a $C_8$ to $C_{25}$ paraffin boiling at a temperature above 140° C, liquid triglycerides or liquid esters of $C_1$ to $C_{12}$ monoalcohols with $C_2$ to $C_{10}$ carboxylic acids, the esters containing at least 8 carbon atoms and at most 12 carbon atoms in the event the ester is of a monobasic acid, and at most 32 carbon atoms in the event the ester is of a dibasic acid or mixtures of said liquid triglycerides with said liquid esters further comprising 0.2 to 5% by weight, based on the total weight percent of the dispersion, of an aluminum chelate of a polynuclear hydroxy-quinone as a stabilizer, said chelate being selected from the group consisting of an aluminum chelate of naphthazarin, quinizarin, chrysazim and alizarin.

2. The fungicidal dispersion as claimed in claim 1, wherein the paraffin boils above 260° C.

3. The fungicidal dispersion as claimed in claim 1, wherein the liquid ester is a diester of phthalic acid.

4. The fungicidal dispersion as claimed in claim 1, wherein the diester is phthalic acid diisooctyl ester.

5. The fungicidal dispersion as claimed in claim 1, wherein the aluminum chelate of a hydroxy-quinone is an aluminum chelate of alizarin.

6. The fungicidal dispersion as claimed in claim 1, wherein the chelate content is in the range of from 0.4 to 2% by weight based on the total weight percent of the dispersion.

7. The fungicidal dispersion as claimed in claim 1, wherein the aluminum chelate is incorporated in situ by the addition of said hydroxy-quinone and an aluminum precursor of said chelate.

8. The fungicidal dispersion as claimed in claim 1, containing up to 20% by weight of an emulsifier and up to 5% by weight of wetting agent or adhesive, the precentages being calculated on the weight percent on said dispersion.

* * * * *